(12) United States Patent
Gavironda

(10) Patent No.: US 12,016,763 B2
(45) Date of Patent: Jun. 25, 2024

(54) UNFOLDABLE FEMININE SANITARY TOWEL

(71) Applicant: Marlon Jesús Gavironda, Oviedo (ES)

(72) Inventor: Marlon Jesús Gavironda, Oviedo (ES)

( * ) Notice: Subject to any disclaimer, the term of this patent is extended or adjusted under 35 U.S.C. 154(b) by 618 days.

(21) Appl. No.: 17/295,642

(22) PCT Filed: Dec. 4, 2018

(86) PCT No.: PCT/ES2018/070779
§ 371 (c)(1),
(2) Date: May 20, 2021

(87) PCT Pub. No.: WO2020/104710
PCT Pub. Date: May 28, 2020

(65) Prior Publication Data
US 2022/0000684 A1 Jan. 6, 2022

(30) Foreign Application Priority Data
Nov. 23, 2018 (ES) ................................ ES201831139

(51) Int. Cl.
*A61F 13/66* (2006.01)
*A61F 13/472* (2006.01)
(Continued)

(52) U.S. Cl.
CPC .......... *A61F 13/665* (2013.01); *A61F 13/472* (2013.01); *A61F 13/5605* (2013.01);
(Continued)

(58) Field of Classification Search
CPC ...... A61F 13/5605; A61F 13/56; A61F 13/70; A61F 13/15; A61F 13/472; A61F 13/665; A41B 9/00
(Continued)

(56) References Cited

U.S. PATENT DOCUMENTS 1,159,362 A * 11/1915 Cornell ................... A61F 13/64
604/401
1,429,510 A * 9/1922 La Maida ................. A61F 5/40
602/73
(Continued)

FOREIGN PATENT DOCUMENTS

CH 259957 A * 2/1949
CN 1432351 A * 7/2003 ........... A61F 13/474
(Continued)

*Primary Examiner* — Benjamin J Klein
*Assistant Examiner* — Gabriella E Burnette
(74) *Attorney, Agent, or Firm* — The Webb Law Firm

(57) ABSTRACT

The invention relates to a sanitary towel element comprising a first laminar body and a second laminar body, wherein the two laminar bodies are joined in opposition to opposite end parts inside end cavities included in the sanitary towel element. In a folded position, the two laminar bodies are located inside the end cavities that communicate with the outside through cuts located in an exterior laminar piece that forms part of the sanitary towel element. In turn, end sections opposite the first laminar body and end sections opposite the second laminar body include coupling devices configured to fasten the feminine sanitary towel around a part of the woman's body in an unfolded use position of the feminine sanitary towel.

3 Claims, 5 Drawing Sheets

(51) Int. Cl.
  *A61F 13/56* (2006.01)
  *A61F 13/70* (2006.01)
  *A61F 13/74* (2006.01)
  *A61F 13/82* (2006.01)

(52) U.S. Cl.
  CPC .............. *A61F 13/70* (2013.01); *A61F 13/74* (2013.01); *A61F 13/82* (2013.01)

(58) Field of Classification Search
  USPC ............ 2/408, 406, 400, 267, 78.2, 113, 70; 450/57
  See application file for complete search history.

(56) References Cited

U.S. PATENT DOCUMENTS

| | | | | |
|---|---|---|---|---|
| 1,508,740 | A * | 9/1924 | Brand | A61F 13/665 604/397 |
| 1,646,880 | A * | 10/1927 | Schaffer | A61F 13/64 604/359 |
| 1,705,194 | A * | 3/1929 | Marinsky | A61F 13/64 604/402 |
| 1,959,282 | A * | 5/1934 | Bade | A61F 13/64 604/401 |
| 2,082,276 | A * | 6/1937 | De Ville | A61F 13/665 604/397 |
| D121,647 | S * | 7/1940 | Coleman | D24/126 |
| 2,206,412 | A * | 7/1940 | Levy | A41B 9/002 2/46 |
| 2,551,663 | A * | 5/1951 | Fox | A61F 13/15268 4/456 |
| 2,700,974 | A * | 2/1955 | Roberts | A61F 13/4755 604/397 |
| 2,881,761 | A * | 4/1959 | Kenner | A61F 13/64 604/397 |
| 2,928,394 | A * | 3/1960 | Roberts | A61F 13/64 604/397 |
| 2,951,481 | A * | 9/1960 | Gordon | A61F 13/74 2/403 |
| 3,094,990 | A * | 6/1963 | Neilson | A41B 9/008 2/400 |
| 3,370,590 | A * | 2/1968 | George | D21H 17/22 162/158 |
| 3,554,196 | A * | 1/1971 | Wargo | A61F 13/64 604/402 |
| 3,635,221 | A * | 1/1972 | Champaigne, Jr. | A61F 13/505 604/394 |
| 4,022,212 | A * | 5/1977 | Lovison | A61F 13/70 604/391 |
| 4,838,886 | A * | 6/1989 | Kent | A61F 13/49004 2/919 |
| 4,905,323 | A * | 3/1990 | Lampman | A41B 9/008 2/46 |
| 5,135,522 | A * | 8/1992 | Fahrenkrug | A61F 13/64 604/401 |
| 5,193,225 | A * | 3/1993 | Karami | A61F 13/64 2/221 |
| 5,441,493 | A | 8/1995 | Gonzalez-Anguiano Marsel et al. | |
| D395,735 | S * | 7/1998 | Paramore | D2/711 |
| 6,572,601 | B2 * | 6/2003 | Suprise | A61F 13/49014 604/391 |
| 7,100,213 | B2 * | 9/2006 | Krautbauer | A41B 9/001 2/403 |
| 7,211,072 | B2 * | 5/2007 | Nawata | A61F 13/68 604/385.03 |
| 7,320,684 | B2 * | 1/2008 | LaVon | A61F 13/5622 604/392 |
| 7,404,216 | B1 * | 7/2008 | Paramore | A63B 71/1216 602/67 |
| 8,603,062 | B1 * | 12/2013 | Smith | A61F 13/491 604/387 |
| 11,517,055 | B1 * | 12/2022 | Cristiano | A41B 9/002 |
| 2004/0267225 | A1 * | 12/2004 | Gandemo | A61F 13/70 604/387 |
| 2005/0256497 | A1 * | 11/2005 | Gottwald | A61F 13/74 604/386 |
| 2009/0018520 | A1 * | 1/2009 | Tachibana | A61F 13/5622 604/385.01 |
| 2009/0131902 | A1 * | 5/2009 | Giloh | A61F 13/70 604/386 |
| 2010/0125264 | A1 | 5/2010 | Naylor | |
| 2012/0209237 | A1 * | 8/2012 | Paz | A61F 13/70 604/392 |
| 2014/0303589 | A1 * | 10/2014 | Paz | A61F 13/15 604/395 |
| 2022/0000684 | A1 * | 1/2022 | Gavironda | A61F 13/5605 |

FOREIGN PATENT DOCUMENTS

| | | | |
|---|---|---|---|
| DE | 662884 C * | 12/1938 | |
| ES | 1008415 U | 4/1989 | |
| ES | 1027634 U | 9/1994 | |
| ES | 1050184 U | 3/2002 | |
| FR | 1307559 A * | 10/1962 | |
| GB | 862763 A * | 3/1961 | |
| KR | 20110049660 A * | 5/2011 | |
| WO | 2005025445 A2 | 3/2005 | |
| WO | WO-2005025445 A2 * | 3/2005 | ........ A61F 13/47218 |

* cited by examiner

UNFOLDABLE FEMININE SANITARY TOWEL

CROSS-REFERENCE TO RELATED APPLICATIONS

This application is the United States national phase of International Application No. PCT/ES2018/070779 filed Dec. 4, 2018, and claims priority to Spanish Patent Application No. P201831139 filed Nov. 23, 2018, the disclosures of which are hereby incorporated by reference in their entirety.

BACKGROUND OF THE INVENTION

Field of the Invention

The present invention relates to an unfoldable feminine sanitary towel comprising a foldable panty structure formed by a sanitary towel element and two bodies joined in opposition to opposite end parts of the sanitary towel element; wherein the garment can be used in the folded position as a sanitary towel element per se in order to be fastened to a second undergarment such as a pair of panties; and wherein the feminine sanitary towel can be used in an unfolded position as a pair of panties per se with the incorporation of the sanitary towel element; where it must be emphasized that in all cases the feminine sanitary towel is disposable.

Description of Related Art

Feminine undergarments are known at present, and among them sanitary towels should be highlighted, such that a number of sanitary towel models are known, some of them having fixing means for being securely fastened to another additional undergarment, such as a pair of panties, such that in all cases an additional undergarment is required to be able to fasten the sanitary towel.

Likewise, there are disposable underwear items on the market with a built-in sanitary towel as a single garment, such as International Patent Application Publication No. WO 2005025445 A2 which relates to a feminine undergarment with an integrated sanitary napkin; wherein the napkin constitutes a sanitary towel element per se.

These products have some limitations, such that in the case of the disposable undergarment with the built-in sanitary towel described in the preceding paragraph, it is done in practice exclusively with the use of a sanitary towel alone. That is, when the user wears the disposable underwear with a sanitary towel, she no longer has the option of using just the sanitary towel if so desired as a single piece.

SUMMARY OF THE INVENTION

For the purpose of achieving the objectives and avoiding the drawbacks mentioned in the preceding sections, the proposed solution is an unfoldable feminine sanitary towel comprising a sanitary towel element, a first laminar body and a second laminar body.

The first laminar body and the second laminar body are joined in opposition to opposite end parts of the sanitary towel element inside end cavities included in said sanitary towel element; wherein the first laminar body and the second laminar body are located inside the end cavities in folded positions of the first laminar body and of the second laminar body.

The end cavities communicate with the outside through cuts located in an exterior laminar piece that forms part of the sanitary towel element.

End sections opposite the first laminar body and end sections opposite the second laminar body include coupling devices configured to fasten the feminine sanitary towel around a part of the woman's body in an unfolded use position of the feminine sanitary towel.

The coupling devices comprise adhesive tapes and through holes; wherein the adhesive tapes are integral with the end sections of the first laminar body, while the through holes are located at the end sections of the second laminar body, such that the adhesive tapes are configured to be introduced into the through holes in the unfolded use position of the feminine sanitary towel.

Moreover, to facilitate the unfolding of the feminine sanitary towel and therefore the unfolding of the two laminar bodies by removing them from the inner spaces of the end cavities, tabs adjacent to the cuts which are integral with the very exterior laminar piece of the sanitary towel element have been provided, such that before removing said laminar bodies, said tabs are pulled on to make the openings demarcated by the cuts made on the exterior laminar piece larger, and thereby facilitate the removal of said laminar bodies through the openings demarcated by the edges of the cuts.

Once the adhesive tapes have been introduced through the through holes, said adhesive tapes are folded over themselves, forming pairs of branches that are joined to one another upon contacting the adhesive material of the branches of said adhesive tapes.

Therefore, the unfoldable feminine sanitary towel of the invention is to be used for intimate feminine hygiene, is disposable and can be converted into an item of feminine underclothing when it is in the unfolded position (with the sanitary towel element included).

The concept of the unfoldable feminine sanitary towel of the proposed solution basically consists of the sanitary towel element with its two end cavities that communicate with the outside through the cuts of the exterior laminar piece, such that by means of portions that form part of the first laminar body and second laminar body, the feminine sanitary towel can be unfolded by pulling on said portions that emerge out through the cuts of the exterior laminar piece of the sanitary towel element.

Therefore, in the unfolded position of the sanitary towel of the invention, said sanitary towel can be used as an item of underclothing and be joined by means of the two adhesive tapes similar to a baby's diaper.

The feminine undergarment can be used as a normal sanitary towel in the folded position and as an item of underclothing in an unfolded position. It can even be used as a panty structure (unfolded position) with underclothing on top of it as well if so desired. As it can be directly used in an unfolded position without underclothing, it replaces conventional underwear, thereby preventing the washing thereof since the undergarment of the proposed solution is disposable and not reusable.

The unfoldable feminine sanitary towel offers the simultaneous option of using the garment as just a sanitary towel adhered to feminine underclothing (panties) preferred by the user, or of unfolding from the inner part (end cavities) of the sanitary towel element the parts (first laminar body and second laminar body) forming the disposable panties and using it, dispensing with wearing complementary underwear by virtue of the security and comfort the unfoldable feminine sanitary towel presents.

The unfoldable feminine sanitary towel includes in the inner part (end cavities) of its end sections, in a folded or gathered form, the first laminar body and the second laminar body. These two bodies may be unfolded, at the discretion of the user, by pulling on the portions initially located (in the folded position of the feminine sanitary towel) at the two opposite ends of the sanitary towel element, which said portions are emerging out through the cuts of the exterior laminar piece of the sanitary towel element, such that when said portions are pulled, they take along with them out of the sanitary towel element the two laminar bodies which form as a whole the disposable garment. Once the first laminar body and the second laminar body (front and rear) have been unfolded, both laminar bodies are fitted around the waist of the user by means of the coupling devices included in the two laminar bodies.

Besides the advantage of the dual use of the sanitary towel of the proposed solution, it offers the advantage of additional training and security for young girls starting with their first menstruations who, given their inexperience, may be prone to have accidents on those days.

The sanitary towel of the proposed solution also provides the possibility of caring for underclothing used on a daily basis because the option of being used without wearing non-disposable underclothing is possible, such that it can be changed as many times as desired without the user having to take off the clothes she is wearing, that is, without taking off her pants, pantyhose, etc. Furthermore, it saves in having to use products for cleaning undergarments as a result of the sanitary towel of the invention being disposable.

With respect to the configuration of the disposable feminine sanitary towel, anatomical aspects are taken into account, as well as making it a stylized undergarment distanced from other conventional disposable undergarment designs.

During a menstrual period with variable flow intensity, the user can have the option at any time during that menstrual period of using the sanitary towel at her discretion and/or according to her needs without unfolding said sanitary towel; and the user can then even change the use of the sanitary towel to the unfolded position.

In cases of periods of travel with hygiene and clothes washing limitations, the sanitary towel can be used interchangeably: in the folded position or in an unfolded position. It should likewise be pointed out that in cases of unexpected trips, there is no need for expenses involved in purchasing sanitary towels and underwear; it can also be applied in some post-operative processes.

The proposed solution also stands out due to the peace of mind owing to discretion and idiosyncrasy, for the ease of purchasing the presentation in sanitary towels, for being common and necessary, and not a disposable undergarment, urine loss products, etc., the modality or use of which is confined to the intimacy and secrecy of the user seeking a certain level of privacy as it is more embarrassing, which is not compromised in this case.

Next, to help better understand this specification and as an integral part thereof, a series of figures is attached in which the object of the proposed solution is depicted in an illustrative and non-limiting manner.

DETAILED DESCRIPTION OF THE INVENTION

Figure 1:
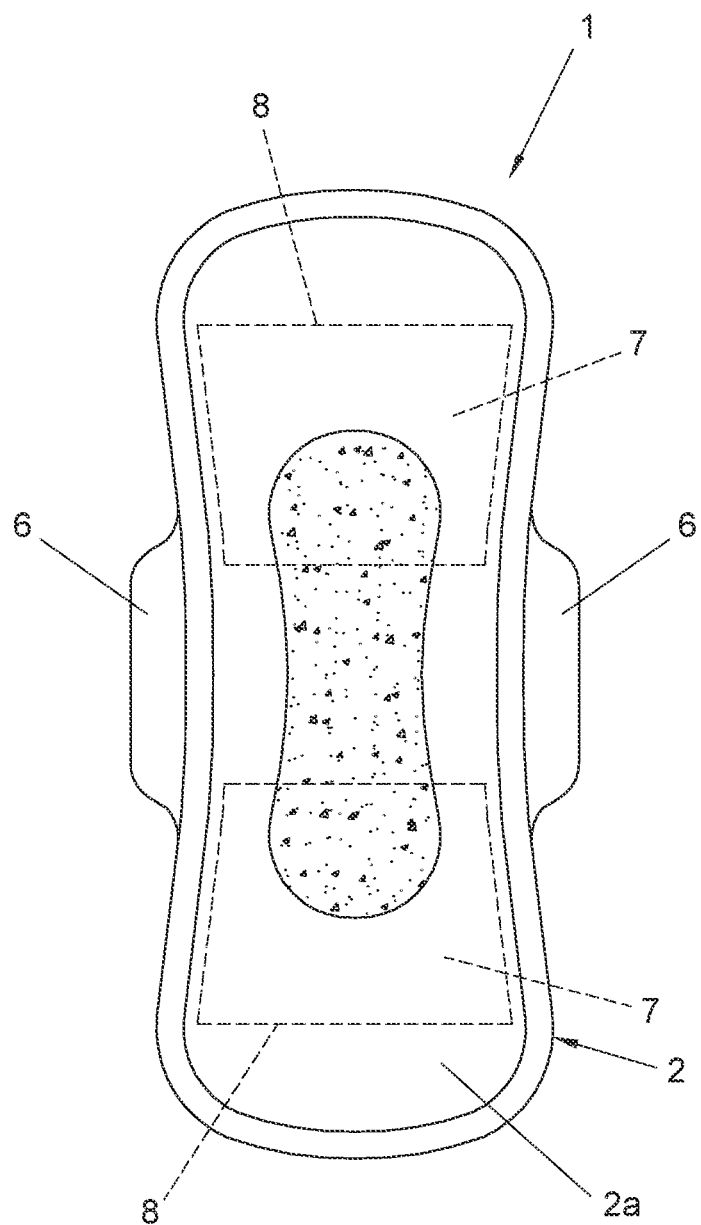
FIG. 1 shows a plan view of the unfoldable feminine sanitary towel, object of the invention. This figure shows the feminine sanitary towel in a folded position, wherein a sanitary towel element shows a first face configured to be in contact with a woman's skin.
Figure 2:
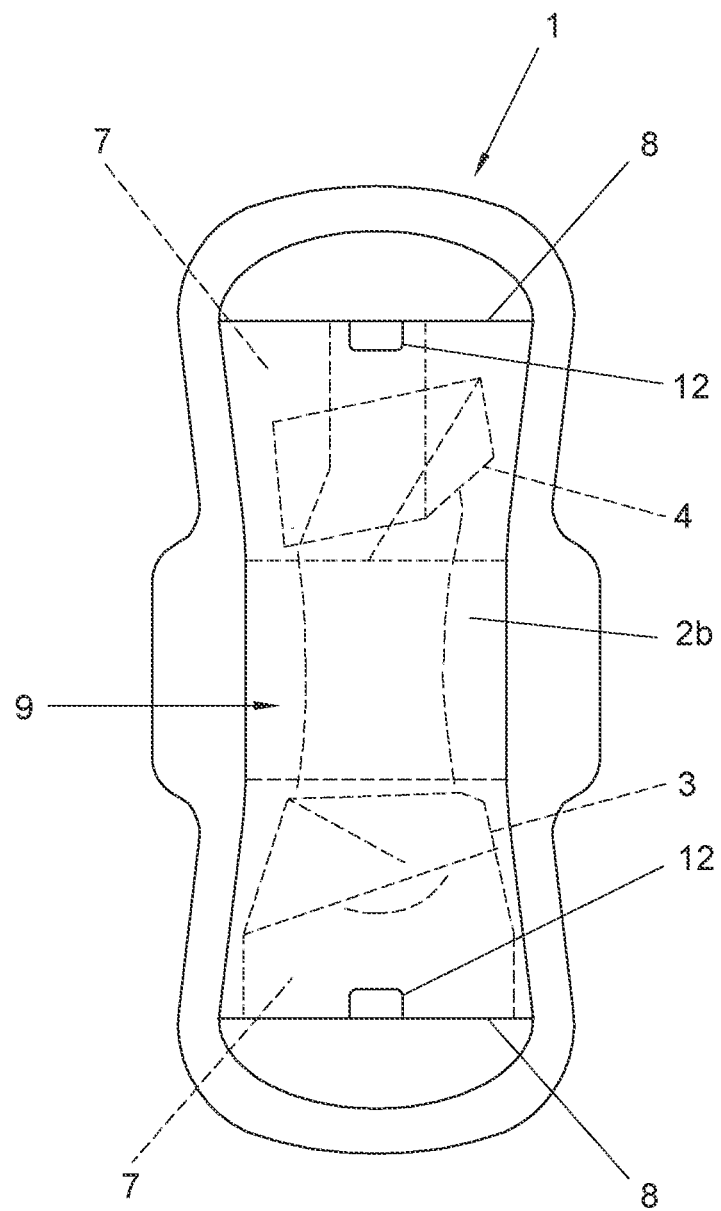
FIG. 2 shows a view of the feminine undergarment in the folded position, wherein tabs integral with an exterior laminar piece of the sanitary towel element are shown; wherein said laminar piece includes cuts and a second face opposite the first face of the sanitary towel element.
Figure 3:
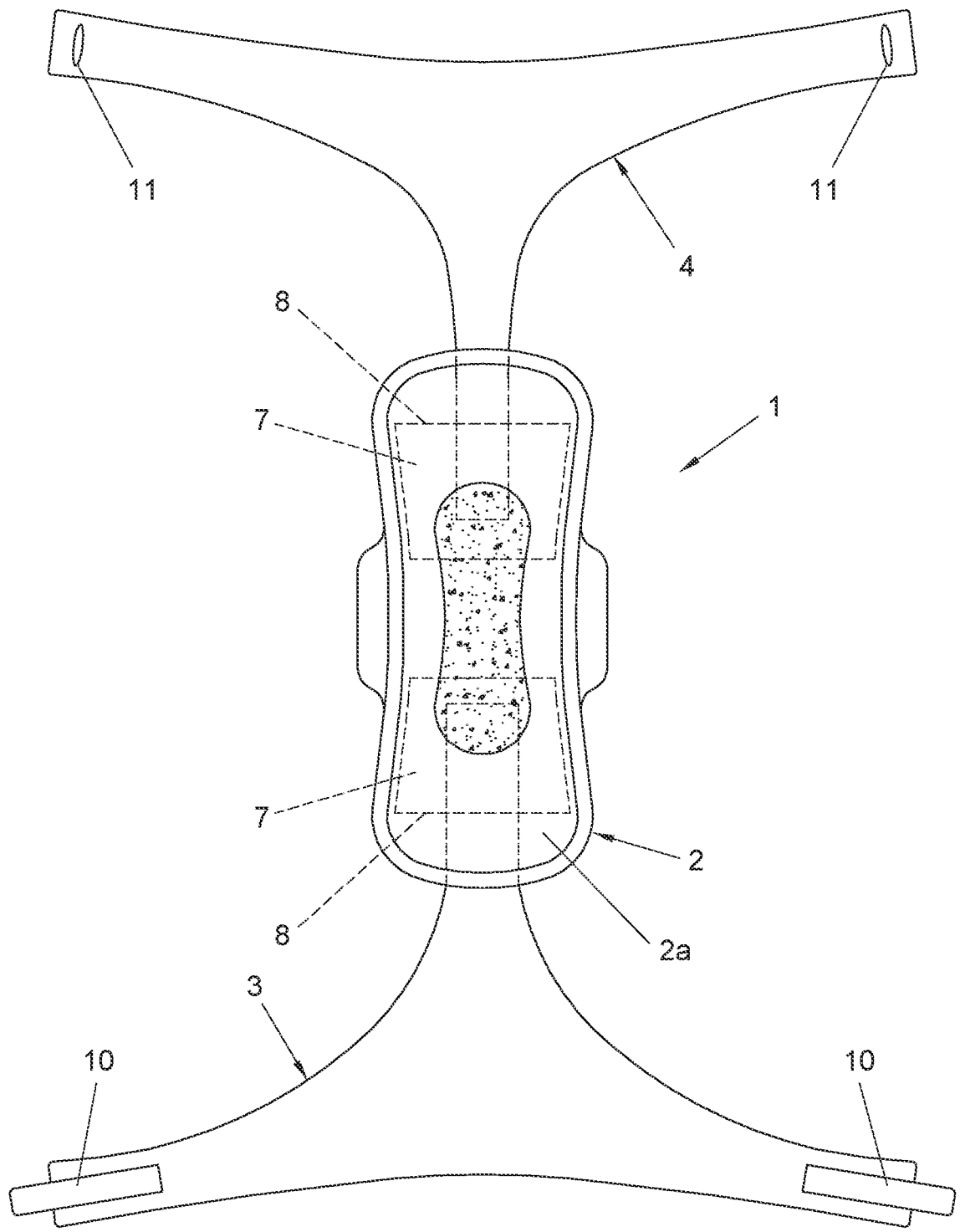
FIG. 3 shows another plan view of the feminine undergarment in an unfolded position; wherein the sanitary towel element shows the first face thereof.
Figure 4:
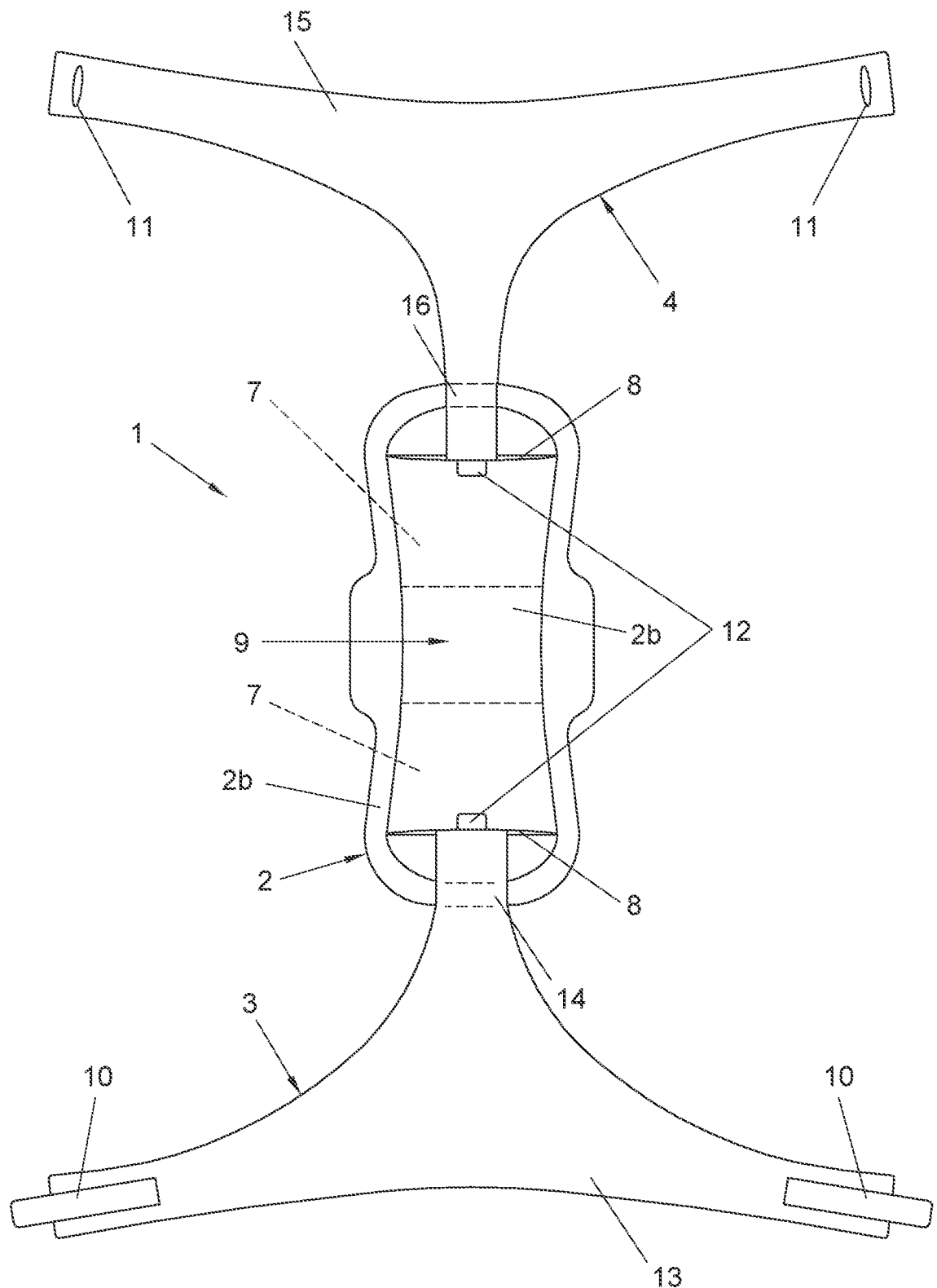
FIG. 4 shows a plan view of the feminine undergarment in an unfolded position; wherein the sanitary towel element shows the second face thereof which is opposite the first face.

Considering the numbers used in the figures, the unfoldable feminine sanitary towel 1 comprises a foldable underwear structure formed by a sanitary towel element 2, a first laminar body 3 and a second laminar body 4 which are located in opposition in correspondence with opposite end parts of the sanitary towel element 2.

The sanitary towel element 2 includes a first face 2a configured to be in contact with a woman's body 5, and a second face 2b opposite the first face 2a.

The undergarment can take a folded position, occupying a small space, and an unfolded position, such that the feminine sanitary towel 1 can be used in the two described positions.

In one embodiment of the invention, when the feminine sanitary towel 1 is used as a sanitary towel per se in the folded position, the first face 2a of the sanitary towel element 2 is in contact with the skin of the woman's body 5. In this case, the feminine sanitary towel 1 is fastened to part of a feminine undergarment such as a pair of panties, such that the fastening of the sanitary towel to the panties is done through side wings 6 in opposition that form part of the sanitary towel element 2.

The sanitary towel element 2 includes two end cavities 7 in opposition for housing in their inner spaces, in folded positions, both the first laminar body 3 and the second laminar body 4; wherein said end cavities 7 are located at end regions of the sanitary towel element 2.

The end cavities 7 of the sanitary towel element 2 communicate with the outside through cuts 8 constituting openings to be able to remove the first laminar body 3 and the second laminar body 4 in order to transform the feminine sanitary towel 1 into an undergarment structure, such as a panty structure. The first laminar body 3 may include a waist end 13 and a sanitary towel end 14. The second laminar body 4 may include a waist end 15 and a sanitary towel end 16.

Said cuts 8 are made on an exterior laminar piece 9 that forms part of the sanitary towel element 2, such that said exterior laminar piece 9 includes the second face 2b opposite the first face 2a of the sanitary towel element 2.

In one embodiment of the process of manufacturing the sanitary towel of the invention, the cuts 8 can also be used for introducing through the first body 3 and the second body 4 with the corresponding fold lines made in said bodies 3, 4.

The feminine sanitary towel 1 comes in the described folded position, such that when it is going to be used, in a first option, it can be used directly by maintaining the folded position as described above. In a second option, the feminine sanitary towel 1 can be used by first unfolding it and then taking a panty structure configuration, as described below.

Figure 5:
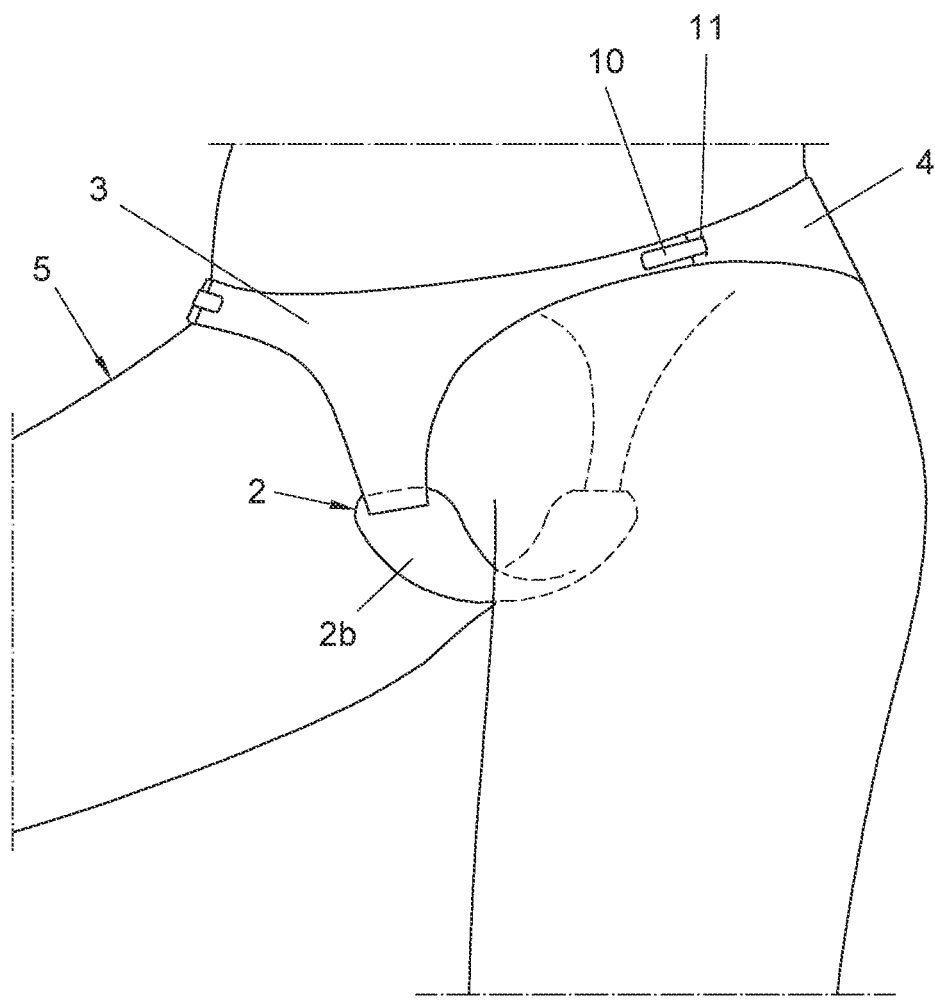
FIG. 5 shows a perspective view of the feminine undergarment in a use position applied on a woman's body.

Therefore, in the unfolded position of the feminine sanitary towel 1, the first laminar body 3 and the second laminar body 4 take a configuration drawn out of the end cavities 7 as a continuation of the ends of the sanitary towel element 2; wherein end sections opposite the first body 3 and end sections opposite the second body 4 include coupling devices for securing the fastening of the unfolded assembly of the feminine sanitary towel 1 around a part of the woman's body 5 in an unfolded use position in correspondence with the two sides of her hips, as shown in FIG. 5, such that the end sections opposite the first body 3 are joined to the end sections opposite the second body 4 by means of the coupling devices.

To carry out the process of unfolding the feminine sanitary towel 1, in a first phase the user uses her hand to pull on portions that form part of the first body 3 and of the second body 4; wherein said portions emerge out of the end cavities 7 through the cuts 8 of the exterior laminar piece 9 that forms part of the sanitary towel element 2, such that when said portions are pulled, the first laminar body 3 and the second laminar body 4 are removed and unfolded until being completely unfolded outside of the end cavities 7 of the sanitary towel element 2.

When the feminine undergarment is used in the unfolded position, the first face 2a of the sanitary towel element 2 is obviously also in contact with the skin of the woman's body 5.

In the embodiment shown in the figures, the coupling devices comprise adhesive tapes 10 and through holes 11, such that the adhesive tapes 10 are configured to be introduced initially through the through holes 11, and once they are introduced, the adhesive tapes 10 are folded over themselves forming two branches which are joined to one another upon contacting the adhesive material of said adhesive tapes 10.

Each pair of branches of each of the adhesive tapes 10 converge in a common section which couples on one portion of the perimetral edge demarcating the respective through hole 11.

If the user were to decide to use only the feminine sanitary towel 1 in a conventional manner, she could adhere the feminine sanitary towel 1 in the folded position through an adhesive system of the type known on the market, such as the side wings 6 shown in FIG. 1.

Moreover, to facilitate unfolding the feminine sanitary towel 1 and therefore the unfolding of the two laminar bodies 3, 4 by removing them from the inner spaces of the end cavities 7, tabs 12 adjacent to the cuts 8 which are integral with the very exterior laminar piece 9 of the sanitary towel element 2 have been provided, such that before removing said laminar bodies 3, 4, said tabs 12 are pulled on to make the openings demarcated by the cuts 8 made on the exterior laminar piece 9 larger, and thereby the removal of said laminar bodies 3, 4 through the openings demarcated by the edges of the cuts 8 is facilitated.

The invention claimed is:

1. An unfoldable feminine sanitary towel, comprising:
a sanitary towel element having an exterior laminar piece with a first end part having a first cut so as to create a first end cavity, and a second end part opposite the first end part having a second cut to as to create a second end cavity;
a first laminar body and a second laminar body, wherein each of the first and second laminar bodies has a waist end and a sanitary towel end, wherein the sanitary towel ends are joined in opposition to the first end part and the second end part, respectively, of the sanitary towel element inside the first and second end cavities of the sanitary towel element; wherein the first end cavity and the second end cavity are configured for housing the first laminar body and the second laminar body, respectively, in a folded position; and wherein the first and second end cavities communicate with the outside through openings demarcated by the edges of cuts located in the exterior laminar piece of the sanitary towel element; and
at least one waist end section of the first laminar body and at least one waist end section of the second laminar body, includes coupling devices configured to fasten the feminine sanitary towel around a part of a woman's body in an unfolded position.

2. The unfoldable feminine sanitary towel according to claim 1, further comprising a plurality of tabs adjacent to the first and second cuts of the exterior laminar piece; wherein the plurality of tabs are integral with the exterior laminar piece of the sanitary towel element.

3. The unfoldable feminine sanitary towel according to claim 1, wherein the coupling devices comprise adhesive tapes and through holes; wherein the adhesive tapes are integral with the at least one waist end section of the first laminar body; wherein the through holes are located at the at least one waist end section of the second laminar body; and wherein the adhesive tapes are configured to be introduced into the through holes in the unfolded position.

* * * * *

UNITED STATES PATENT AND TRADEMARK OFFICE
CERTIFICATE OF CORRECTION

Page 1 of 1

PATENT NO. : 12,016,763 B2
APPLICATION NO. : 17/295642
DATED : June 25, 2024
INVENTOR(S) : Marlon Jesús Gavironda It is certified that error appears in the above-identified patent and that said Letters Patent is hereby corrected as shown below:

On the Title Page

Column 1, Foreign Application Priority Data, Line 1, delete "ES201831139" and insert -- P201831139 --

Signed and Sealed this
Fifteenth Day of July, 2025

Coke Morgan Stewart
*Acting Director of the United States Patent and Trademark Office*